United States Patent [19]

Stallman

[11] Patent Number: 5,763,661
[45] Date of Patent: Jun. 9, 1998

[54] PREPARATION OF ACYLATED α-AMINO CARBOXYLIC ACID AMIDES

[75] Inventor: John B. Stallman, Amherst, N.H.

[73] Assignee: Hampshire Chemical Corp., Lexington, Mass.

[21] Appl. No.: 783,924

[22] Filed: Jan. 17, 1997

[51] Int. Cl.$^6$ .................................................. C07C 231/06
[52] U.S. Cl. .................. 564/124; 564/126; 564/129; 564/130; 564/142; 564/143; 564/152
[58] Field of Search .................... 564/124, 126, 564/129, 130, 142, 143, 152

[56] References Cited

U.S. PATENT DOCUMENTS

| | | | |
|---|---|---|---|
| 5,352,788 | 10/1994 | Bernhart et al. | 544/319 |
| 5,424,450 | 6/1995 | Boswell et al. | 548/253 |

FOREIGN PATENT DOCUMENTS

| | | | |
|---|---|---|---|
| 43-19932 | 8/1943 | Japan | 564/124 |

OTHER PUBLICATIONS

Zhurnal Organ. Khimii, 20(7), pp. 1243–1247 (1984).

J. Org. Chem. 27, p. 798–802 (1962).

*Primary Examiner*—Shailendra Kumar
*Attorney, Agent, or Firm*—Nields, Lemack & Dingman

[57] ABSTRACT

A method of preparing acylated α-amino carboxylic acid amides directly from amino nitriles in high yield and purity. The method involves acylating the amino nitrile with an acyl halide under Schotten-Baumann conditions, and hydrolyzing the resulting nitrile to the amide. The resulting acylated amino carboxylic acid amide precipitates and can be isolated by filtration in high purity.

9 Claims, No Drawings

PREPARATION OF ACYLATED α-AMINO CARBOXYLIC ACID AMIDES

BACKGROUND OF THE INVENTION

The present invention relates to a process for producing acylated α-amino carboxylic acid amides. Such amides are useful as intermediates for N-substituted heterocyclic pharmaceutical compositions useful in the treatment of cardiovascular diseases including hypertension, as well as glaucoma, diabetic retinopathy and renal insufficiency. In particular, the pharmaceutical compositions demonstrate antagonistic action against angiotensin II, a potent vasopressor.

Conventional processes for the preparation of α-amino carboxylic acid amides suffer from various disadvantages, including low yields, low purity, the requirement of many steps in the synthetic route, and complex isolation schemes. Thus, one route to the amides is disclosed in Abramov, et al., *Zhurnal Organ. Khimii*, 20(7), p. 1243–1247 (1984) where the preparation of α-aminoamides and α-amino acids from the corresponding α-aminonitriles using manganese (IV) in the form of manganese oxide is taught. Reaction times are critical, as longer reaction times lead to the amino acid. In addition, reversion to the starting cyanohydrin and ketone can occur.

Another somewhat analogous synthetic scheme is disclosed in Johnson, et al., *J. Org. Chem.* 27, p. 798–802 (1962). This method involves the reaction of an aminonitrile with anhydrous HCl in the presence of an alcohol. The aminonitrile is dissolved in n-butanol and is then treated with anhydrous HCl and stirred at room temperature for 24 hours. The reaction mixture is then refluxed for one hour. The imidate ester hydrochloride is formed as an intermediate, and decomposes upon the application of heat to the corresponding amide and an alkyl chloride.

U.S. Pat. No. 5,352,788 discloses a synthesis that involves the hydrolysis of the oxalate salt of the aminonitrile using concentrated sulfuric acid, followed by treatment with ammonia and then extraction with chloroform containing 5% methanol.

Conventional synthetic routes to the acylated α-amino carboxylic acid amides involves acylating the amide, such as cycloleucine amide, with acyl chloride in THF with triethylamine. However, it would be desirable to eliminate the use of organic solvents and provide a simple, economic process to prepare acylated α-amino carboxylic acid amines directly from the amino nitrile.

It is therefore an object of the present invention to provide a method of producing acylated aminoamides directly from the corresponding amino nitrile.

It is a further object of the present invention to provide a method of producing acylated aminoamides from amino nitrites in high yield and without the concomitant production of potentially hazardous by-products.

It is a still further object of the present invention to provide a method of producing acylated aminoamides from amino nitriles without requiring complex isolation steps.

SUMMARY OF THE INVENTION

The problems of the prior art have been overcome by the present invention, which provides a method of preparing acylated α-amino carboxylic acid amides directly from amino nitriles in high yield and purity. The method involves acylating the amino nitrile with an acyl halide, preferably acyl chloride, under Schotten-Baumann conditions. The resulting acylated amino carboxylic acid amide can be hydrolyzed, precipitated and isolated by filtration in high purity.

DETAILED DESCRIPTION OF THE INVENTION

The amino nitrile can be virtually any α-aminonitrile corresponding to the acylated α-amino carboxylic acid amide desired, and can be prepared from the corresponding ketone or aldehyde by conventional means well known to those skilled in the art. For example, the ketone in a suitable solvent such as methanol can be reacted with an ammonia source (such as ammonia and ammonium chloride) and a cyanide source (such as alkali metal cyanide), and the resulting amino nitrile can be recovered by extraction with methylene chloride and dried. Dialkyl aminonitriles such as acetone aminonitrile, acetophenone aminonitrile, methyl ethyl aminonitrile are suitable, as are monoalkyl aminonitriles such as benzaldehyde aminonitrile and acetaldehyde aminonitrile. N-substituted aminonitriles are also suitable, including N-methyl glycinonitrile, N-butyl aminonitrile and N-phenyl aminonitrile. Cyclopentanone aminonitrile is particularly preferred.

Suitable acyl groups for the acyl halide are straight or branched aliphatic or aromatic groups containing from 1 to 40 carbon atoms, preferably acyl groups that are carboxylic acid derivatives. Examples of preferred acyl groups are valeroyl, pentanoyl, hexanoyl, heptanoyl, octanoyl, nananoyl, decanoyl, lauroyl, myristoyl, palmitoyl, oleoyl, stearoyl, nonanoyl, neopentanoyl, neoheptanoyl, neodecanoy, iso-octanoyl, iso-nananoyl, isotridecanoyl, benzoyl and naphthoyl. Valeryl chloride is particularly preferred.

In accordance with the present invention, the pH of an aqueous solution of the amino nitrile is adjusted within a range of 9–12 (standard Schotten-Baumann conditions) to effect acylation, and the temperature is maintained between about 0° and 30° C., preferably at about 10° C. The amino nitrile should be used in slight excess to the acid halide, preferably 1.05 or less/1.00. Larger excesses of the amino nitrile are operable but wasteful. The acyl halide is slowly added to the amino nitrile aqueous solution at a rate such that the temperature of the reaction medium is kept to 200° C. or lower. The pH of the reaction medium is preferably maintained in the above range, more preferably in a range between 9.5–10.5, by co-feeding base, preferably alkali metal hydroxide, to the reaction medium with the acyl halide. The base serves to scrub the acid (HCl in the case of acyl chloride) generated from the acylation and thus maintain the pH within the operable range. As a result, operable amounts of base will vary depending upon the amount of acid generated, but are generally between 1–2 times the number of equivalents of acid halide. Failure to co-feed the base with the acyl halide results in the hydrolysis of the acyl halide as a competing reaction.

Preferably the reaction is stirred at 20° C. and is held for at least two hours while maintaining the pH within the aforementioned range. Hydrolysis is then carried out by adjusting the pH, preferably to less than about 0.5 with a suitable acid, such as HCl, sulfuric or phosphoric acid, preferably HCl, to hydrolyze the nitrile to the carboxylic acid amide. Higher pH's in the range of 0.5–4 could be used, but result in longer reaction times. Alternatively, hydrolysis could be conducted under basic conditions, such as with the addition of 0.1 to 4 equivalents of alkali metal hydroxide. The reaction is then heated to reflux to affect complete hydrolysis of the nitrile to the carboxylic acid. Temperatures of 30°–1000° C. are suitable, with the higher end of the range being preferred in order to minimize reaction times. Hydrolysis is generally completed in under two hours. The resulting solids (acylated amino carboxylic acid amide) are isolated and can be collected by filtration.

The theoretical reaction mechanism can be illustrated as follows for the preparation of valeryl cycloleucine amide:

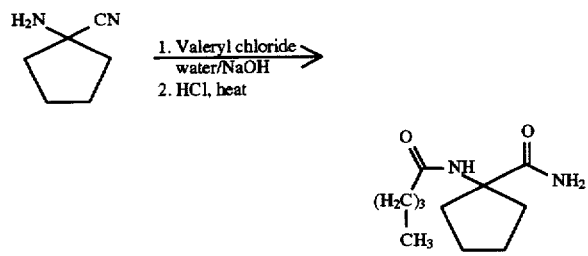

EXAMPLE 1

The amino nitrile of cyclopentanone was prepared using methods commonly found in the literature. The amino nitrile of cyclopentanone (30.00 g, 0.273 mole) and water were added to a 500 ml 5-neck round bottom flask equipped with a mechanical stirrer, a pH meter, a thermometer, and two additional funnels. The pH was then adjusted to 10.00 with 50% NaOH and the reaction cooled to 10° C. Valeryl chloride (31.60 g, 0.262 mole) was then slowly added to the reaction at such a rate as to maintain the temperature at 20° C. or below. The pH of the reaction was maintained from 9.5–10.5 by co-feeding 25% NaOH (10.91 g, 0.272 mol) to the reaction with the valeryl chloride. The reaction was stirred at 20° C. for one hour maintaining a pH of 9.5–10.5 with 25% NaOH. After one hour, the pH was adjusted to 0.5 with concentrated HCl, the reaction heated to reflux for one hour, cooled to room temperature, and the resulting solids collected by filtration.

EXAMPLE 2

The aminonitrile was acylated as described previously on a 0.455 mole scale. 0.437 moles of NaOH (50% aqueous) were then added and the reaction warmed to 70 C. for ten hours. The resulting solution contained approximately a 50% conversion to the valeryl cycloleucine amide.

What is claimed is:

1. A process of preparing an acylated α-aminocarboxylic acid amide, comprising:

preparing an aqueous solution of said α-aminonitrile;

acylating said α-aminonitrile in said aqueous solution by adding an acyl halide and sufficient base to said aqueous solution to maintain the pH of said aqueous solution in the range of 9–12; and hydrolyzing the resulting acylated nitrile to the corresponding carboxylic acid amide by adjusting the pH of said aqueous solution in the range of 0–4 under reflux, said amide precipitating from said aqueous solution upon formation.

2. The process of claim 1, wherein said α-aminonitrile is selected from the group consisting of dialkyl aminonitriles, monoalkyl aminonitriles and N-substituted aminonitriles.

3. The process of claim 1 wherein said α-aminonitrile is cyclopentanone aminonitrile.

4. The process of claim 1 wherein said acyl halide is valeryl chloride.

5. The process of claim 3 wherein said acyl halide is valeryl chloride.

6. The process of claim 1, wherein the pH of the reaction mixture is lowered to less than about 0.5 upon completion of the acylation reaction.

7. The process of claim 1, wherein said base is an alkali metal hydroxide.

8. The process of claim 1, wherein said base is sodium hydroxide.

9. The process of claim 1, wherein said pH is adjusted in the range of 0–4 with hydrochloric acid.

* * * * *